(12) United States Patent
Wischmann et al.

(10) Patent No.: US 8,411,915 B2
(45) Date of Patent: Apr. 2, 2013

(54) MOTION COMPENSATION IN FUNCTIONAL IMAGING

(75) Inventors: Hans-Aloys Wischmann, Henstedt-Ulzburg (DE); Lingxiong Shao, Saratoga, CA (US); Angela Da Silva, Danville, CA (US); Ingwer C. Carlsen, Hamburg, DE (US); Carsten Meyer, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 1304 days.

(21) Appl. No.: 11/997,410

(22) PCT Filed: Jul. 27, 2006

(86) PCT No.: PCT/IB2006/052585
§ 371 (c)(1),
(2), (4) Date: Jan. 31, 2008

(87) PCT Pub. No.: WO2007/015199
PCT Pub. Date: Feb. 8, 2007

(65) Prior Publication Data
US 2008/0226149 A1    Sep. 18, 2008

Related U.S. Application Data

(60) Provisional application No. 60/595,768, filed on Aug. 4, 2005.

(51) Int. Cl.
*G06K 9/00* (2006.01)
(52) U.S. Cl. ........................................ 382/128; 382/131
(58) Field of Classification Search .................. 382/128, 382/131–132; 600/300, 407–481; 702/19–21; 378/4–27
See application file for complete search history.

(56) References Cited

U.S. PATENT DOCUMENTS 5,633,951 A    5/1997  Moshfeghi
5,939,716 A *  8/1999  Neal .............................. 250/251
(Continued)

FOREIGN PATENT DOCUMENTS

EP    1087337 A1    3/2001
GB    2250164 A     5/1992
(Continued)

OTHER PUBLICATIONS

Thinh et al. ("Reconstructing the 3D Medial Axes of Coronary Arteries in Single—View Cineangiograms" IEEE Transactions on Medical Imaging, vol. 13, No. 1, Mar. 1994, pp. 61-74).*

(Continued)

Primary Examiner — Phillip A Johnston
Assistant Examiner — Brooke Purinton

(57) ABSTRACT

Medical images are collected in a plurality of cardiac and respiratory phases. The images are transformed into a series of respiratory compensated images with the plurality of cardiac phases, but all at a common respiration phase. The series of respiratory compensated images are transformed into one image at a selected cardiac phase and the common respiration phase. In some embodiments, a database of gated transform matrices is generated. The database may be based on specific patient information or on information generated from a pool of patients. The database may account for respiratory motion, cardiac contractile motion, other physiological motion, or combinations thereof. For a current image to be motion corrected, the transformation matrices collected in the database are used to estimate a current set of transformation matrices accounting for the motion in the current image, and a motion-compensated image is generated based on the current set of transform matrices.

26 Claims, 4 Drawing Sheets

U.S. PATENT DOCUMENTS

| | | | | |
|---|---|---|---|---|
| 6,067,859 | A * | 5/2000 | Kas et al. | 73/800 |
| 6,228,030 | B1 * | 5/2001 | Urbano et al. | 600/443 |
| 6,473,636 | B1 * | 10/2002 | Wei et al. | 600/436 |
| 7,170,050 | B2 * | 1/2007 | Turner et al. | 250/251 |
| 7,173,248 | B2 * | 2/2007 | Ross et al. | 382/131 |
| 7,180,976 | B2 * | 2/2007 | Wink et al. | 378/8 |
| 7,454,048 | B2 * | 11/2008 | Schoisswohl et al. | 382/131 |
| 7,491,928 | B2 * | 2/2009 | Roichman et al. | 250/251 |
| 7,558,439 | B2 * | 7/2009 | Weese et al. | 382/294 |
| 7,657,069 | B2 * | 2/2010 | Boese et al. | 382/128 |
| 7,693,563 | B2 * | 4/2010 | Suresh et al. | 600/407 |
| 8,005,284 | B2 * | 8/2011 | Sakaguchi et al. | 382/131 |
| 2002/0077546 | A1 * | 6/2002 | Aldefeld et al. | 600/424 |
| 2003/0123606 | A1 * | 7/2003 | Mollus et al. | 378/42 |
| 2004/0089798 | A1 * | 5/2004 | Gruber et al. | 250/251 |
| 2004/0090632 | A1 * | 5/2004 | Dholakia et al. | 356/450 |
| 2004/0207922 | A1 * | 10/2004 | Grier et al. | 359/614 |
| 2004/0208341 | A1 * | 10/2004 | Zhou et al. | 382/103 |
| 2004/0260176 | A1 | 12/2004 | Wollenweber et al. | |
| 2005/0043609 | A1 * | 2/2005 | Murphy et al. | 600/408 |
| 2005/0123183 | A1 * | 6/2005 | Schleyer et al. | 382/131 |
| 2007/0139784 | A1 * | 6/2007 | Roichman et al. | 359/614 |
| 2009/0190221 | A1 * | 7/2009 | Boer et al. | 359/558 |

FOREIGN PATENT DOCUMENTS

| | | |
|---|---|---|
| WO | 9735212 A1 | 9/1997 |
| WO | 2004111946 A1 | 12/2004 |

OTHER PUBLICATIONS

Aggarwal, N., et al.; Spatio-Temporal Modeling and Adaptive Acquisition for Cardiac MRI; 2004; IEEE Intl. Symposium on Biomedical Imaging: Macro to Nano; pp. 628-631.

Debreuve, E., et al.; Nonparametric and nonrigid registration method applied to myocardial-gated SPECT; 2002; IEEE Trans. on Nuclear Science; 49(3)782-788.

McLeish, K., et al.; A study of the motion and deformation of the heart due to respiration; 2002; IEEE Trans. on Medical Imaging; 21(9)1142-1150.

Papademetris, X., et al.; 3D cardiac deformation from ultrasound images; 1999; Proc. of the MICCAI; pp. 420-429.

Ritchie, C. J., et al.; Correction of computed tomography motion artifacts using pixel-specific back-projection; 1996; IEEE Trans. on Medical Imaging; 15(3)333-342.

Zeng, G. L., et al.; Projection data registration for gated cardiac SPECT reconstruction; 2003; IEEE; pp. 1516-1518.

* cited by examiner

MOTION COMPENSATION IN FUNCTIONAL IMAGING

CROSS REFERENCE TO RELATED APPLICATIONS

This application claims the benefit of U.S. provisional application Ser. No. 60/595,768 filed Aug. 4, 2005, which is incorporated herein by reference.

The present invention relates to the digital imaging arts. It finds particular application in conjunction with Single Photon Emission Computed Tomography (SPECT) or Positron Emission Tomography (PET) imaging systems, and more specifically with combined SPECT/CT or PET/CT systems and will be described with particular reference thereto. It is, however, to be appreciated that the invention may also find application in the combination of SPECT, PET, or other nuclear imaging scans, and other modalities, such as CT, MRI, Ultrasound, and others.

In nuclear medicine, a subject is injected with a radiopharmaceutical that carries a radioisotope which decays, emitting gamma radiation. Nuclear cameras, such as SPECT or PET scanners, detect the gamma radiation and reconstruct a diagnostic image illustrating a density of radioactive events in the subject.

In SPECT imaging, a radioactive source emits high energy particles that pass through at least a portion of a subject in an imaging region and are collected at a detector array that is positioned adjacent the subject. In order to receive enough radiation events to reconstruct a meaningful diagnostic image, the subject remains in the imaging region for an extended period of time, on the order of 10 s of minutes or more. Comparatively, a CT scan can perform a complete scan of a limited region in less than a minute.

As the subject has to remain in the imaging region for an extended period of time, several sources of motion occur that will lower the spatial resolution of a resulting image. First, the subject can move. Voluntary movements cause the internal anatomy of the subject to move also, and thus, shift positions in a diagnostic image. Second, the scan time is far too long for a subject to hold their breath. Even shallow, controlled breathing will introduce periodic motion of the chest cavity. Continuous respiration during the SPECT acquisition leads to a periodic translation of the heart by several centimeters in the cranial-caudal direction. This leads to spatial blur of the reconstructed images and degrades the left ventricle volume estimation in both the individual heart phases and the perfusion image.

Imaging many body regions may be difficult or may result in blurring due to body, respiratory, cardiac and other physiological rhythms. For example in cardiac SPECT, images of the heart are being gathered, and naturally, the heart is constantly moving. The beating heart periodically contracts, translates, rotates, and twists which displaces individual segments of the myocardium by several centimeters in a complicated and non-homogeneous fashion. This degrades the spatial resolution of the summed perfusion image. These three sources of motion all produce spatial variance in the position of the internal organs of the subject, and ultimately cause spatial blurring of a resultant SPECT image. As the SPECT modality of imaging improves, these sources of motion will become increasingly problematic because they will negate the advantages gained from higher resolution by blurring the images.

Efforts are currently underway to register voluntary physical patient motion, and compensate for that motion. These efforts, however, currently do not compensate for motion caused by the natural respiratory and cardiac cycles, and only focus on SPECT image space.

The present invention provides a new and improved method and apparatus which overcomes the above-referenced problems and others.

In accordance with one aspect of the present invention, a method of respiratory and cardiac movement compensated diagnostic imaging is provided. A plurality of heart images are generated in each of a plurality of respiratory and cardiac phases with a first imaging modality. The images which have a common cardiac phase but different respiratory phases are transformed into images of the plurality of cardiac phases, but all at a selected common respiratory phase. The images with a common cardiac phase and the selected respiratory phase are combined into a series of respiratory compensated images at the plurality of cardiac phases. The series of respiratory compensated images are transformed in accordance with a heart shape and motion model to generate a series of cardiac and respiratory compensated images all in a selected common cardiac phase and the selected common respiratory phase. These images are combined into an image in the selected common cardiac and respiratory phases.

In accordance with another aspect of the present invention, a method of compensating for respiratory and cardiac movement in diagnostic image reconstruction is provided. The respiratory activity of a subject is monitored during a nuclear imaging scan and a respiratory movement vector is created. Cardiac activity of the subject is also monitored during the scan. Raw image data acquired during the scan is binned in accordance with both its respiratory and cardiac phases and the binned raw data is reconstructed into a plurality of images. The images are translated in accordance with the respiratory movement vector and are further adjusted in accordance with a heart shape and motion model. The translated and adjusted images are then combined.

In accordance with another aspect of the present invention, a diagnostic imaging apparatus is provided. A first modality scanner generates a plurality of heart images in each of a plurality of respiratory and cardiac phases. A respiratory adjustment processor transforms the images which have a common cardiac phase but different respiratory phases into a series of images at the plurality of cardiac phases but at a selected common respiratory phase. A cardiac transforming routine transforms the series of respiratory compensated images in accordance with a heart shape and motion model to generate a series of cardiac and respiratory compensated images at a selected cardiac phase and at the selected common respiratory phase. A cardiac summing routine combines the images and the selected common cardiac and respiratory phases.

In accordance with another aspect of the present invention, an image reconstruction processor is provided for use in conjunction with cardiac SPECT imaging procedures. A respiratory adjustment processor receives a plurality of images of differing respiratory phases and differing cardiac phases and adjusts the images of differing respiratory and cardiac phases into a series of images with a common respiratory phase but the differing cardiac phases. A cardiac adjustment processor receives the series of images and adjusts them into a common cardiac phase to produce an image at the common cardiac phase and a common respiratory phase.

One advantage of the present invention is a more robust estimation of and correction for respiratory motion.

Another advantage of this invention is a more robust estimation of and correction for cardiac motion.

Yet another advantage of this invention resides in the elimination of spatial blur due to respiratory and cardiac motion.

Still further advantages of the present invention will be appreciated to those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

Figure 1:
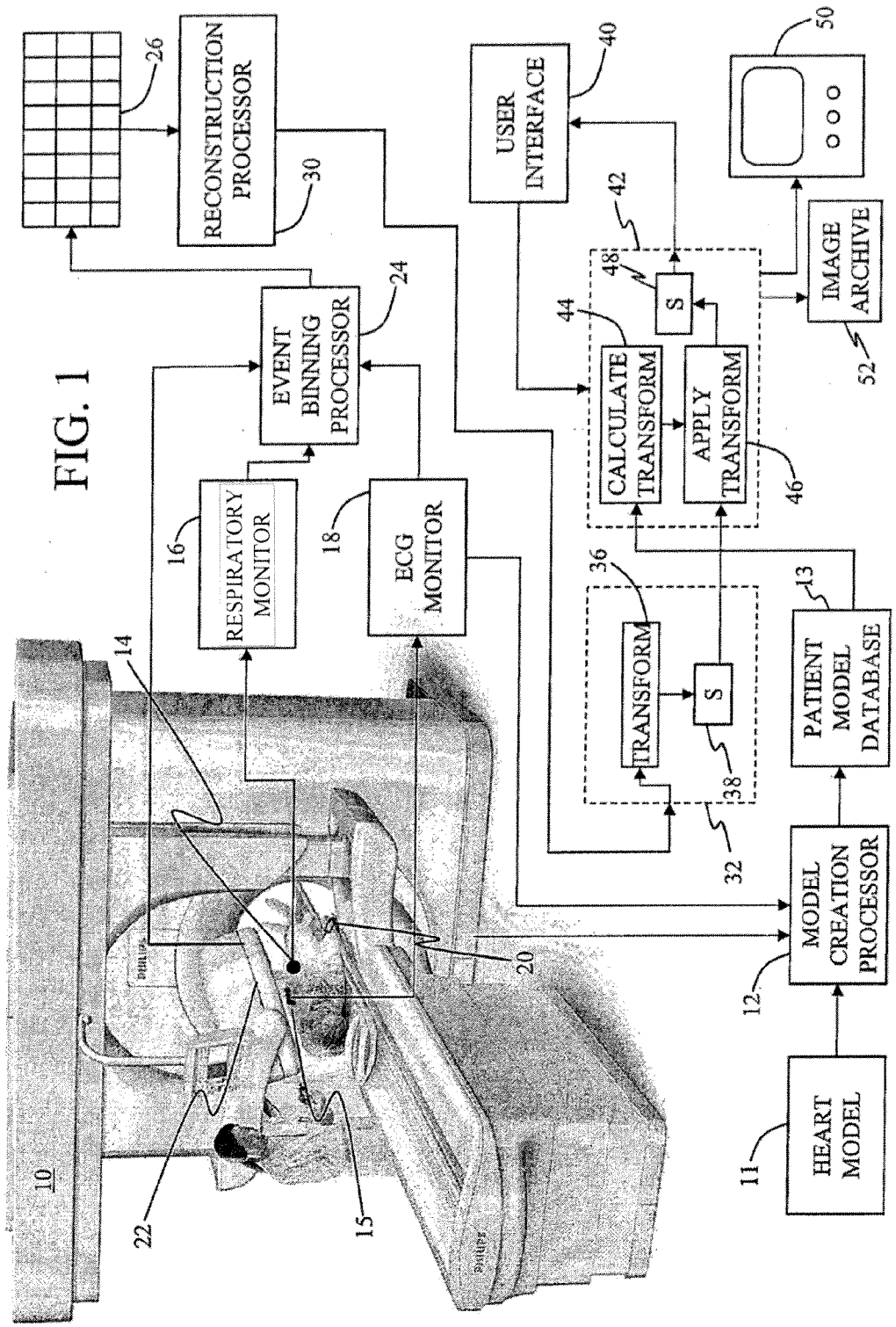
FIG. 1 is a diagrammatic illustration of a SPECT/CT system in accordance with the present invention.

The human heart beats in a predictable fashion. During normal activity, the speed at which the heart beats can vary, from less than once per second when the subject is at rest, up to about three times per second under extreme physical exertion and/or stress. Also, its range of motion is not always exactly the same from person to person. Often, when a subject is scheduled for a cardiac SPECT imaging procedure, the physician is attempting to diagnose cardiac anomalies, and these can often affect how the heart behaves in its cycle.

Resultantly, it is beneficial to perform a preliminary, cardiac modeling scan of the heart to create an individualized cardiac shape and motion model, i.e., a model that is subject-specific. In order to generate the subject-specific heart shape and motion model, with reference to FIG. 1, the subject is positioned in a diagnostic scanner 10. A modeling scan is performed that captures images at several phases, e.g. 5-10 phases, of the cardiac cycle and are collected during a breath hold period to be free of respiratory motion degradation. Alternately, gated acquisitions or reconstructions can be used to generate cardiac images in a common respiratory phase. Optimally, these images capture and display translation, rotation, stretching, contracting, and warping of the heart muscle during its cycle. Preferably, the diagnostic scanner 10 is a combined SPECT/CT scanner and the cardiac modeling scan is performed on a CT portion. This allows two types of diagnostic scans to be performed sequentially without the subject moving. Of course, separate scanners are contemplated, but in such a case, the subject is relocated, and re-positioned to duplicate the position of the cardiac modeling scan. The modeling scan performed is preferably an ECG gated CT scan. ECG gating ensures that the desired images of each stage of heart motion are captured.

Preferably, the cardiac modeling scan is performed immediately before the SPECT imaging scan. This is to ensure maximum consistency between the subject's cardiac behavior from the cardiac modeling scan to the SPECT scan. Alternatively, the cardiac modeling scan can be performed on a different day, for example, but in this case it is more likely that cardiac behavior will have changed. This is more of a concern with subjects with known heart defects, because it is more likely that the subject's heart will vary its activity pattern over time. Also, the cardiac modeling scanner does not have to be a CT scanner, but can also be MRI, ultrasound, Doppler ultrasound, or any other modality that can reliably capture the complete range of motion of the heart from an anatomical standpoint.

After the cardiac modeling scan is performed, a model creation processor 12 fits a generic heart shape and motion model 11 to the patient-specific data that was just acquired, e.g. by adapting or fitting the shape model to the individual images reconstructed for the different cardiac phases. The motion part of the heart shape and motion model can be used to guide or regularize this adaptation procedure. A patient-specific motion map for the myocardium is then derived from point correspondences of the fitted models, which yields a robust estimate. Clinicians have identified at least eight different points within a cardiac cycle where the heart is in a different position. The generic model represents expected positions for the average heart. By fitting the expected motion of the generic model to the actual motion of the subject's heart gathered from the cardiac modeling scan, a patient-specific heart model is obtained. It is preferred that the model illustrate the position of the subject's heart in at least eight phases, but more or fewer phases are contemplated. With fewer phases, the model may not capture the full range of motion of the heart.

The patient specific shape and motion model is then stored in a patient model database 13. The patient specific cardiac models can be stored for an indeterminate length of time, so that any subsequent SPECT imaging procedure for that patient may call upon them. Periodically, new patient specific models can be generated to replace old ones if the patient is slated to have several SPECT scans or the condition of the heart changes. Similarly, models stored within the database 13 can be marked as out of date, or deleted entirely. It may, however, be beneficial to archive old patient specific models to compare to newer ones, as an additional diagnostic tool showing how heart function changes over time.

Once the patient-specific heart model is generated and stored, the subject is ready for the SPECT imaging procedure. If a SPECT/CT scanner was used to create the cardiac model, then the patient support translates the region of interest from the CT gantry portion to the SPECT gantry portion. In preparation for the scan, the subject is outfitted with a respiratory motion sensor 14, such as an optical marker mounted near the diaphragm and a marker position monitor such as a video system. RF systems, acoustic systems, other optical systems, pneumatic systems, and the like are also contemplated. The sensor 14 is positioned adjacent the subject's diaphragm, to detect the periodic motion of the subject's respiratory cycle. In particular, the sensor 14 is positioned such that at least a position of maximum inhale and a position of maximum exhale are detected. Preferably, an intermediate respiratory position is sensed midway between maximum inhale and maximum exhale. A total of three respiratory positions is preferred including the two extreme positions. Additional intermediate respiratory positions can be generated, event counts permitting.

In addition to connecting the subject with the respiratory sensor 14, cardiac ECG electrodes 15 are applied to the subject. If the cardiac modeling scan was just performed, then the subject will already have the ECG electrodes 15 attached. Once both the cardiac and respiratory sensors are in place, the subject is ready for nuclear scanning. A respiratory monitor 16 tracks the respiratory cycle, and an ECG monitor 18 tracks the cardiac cycle during nuclear imaging.

The subject is injected with a radioactive substance 20. Common radionuclides used in nuclear medicine (SPECT and PET) include technetium-99m, thallium-201, fluorine-18, indium-111, gallium-67, iodine-123, iodine-131, and xenon-133. Typically, each radionuclide is coupled with a carrier molecule targeted to a specific cellular process. For myocardial perfusion studies, the carriers that concentrate in the bloodstream are selected. The carrier molecules tend to accumulate at the area of interest, and the radionuclide decay provides information about the location and concentration of carriers, hence the location of blood, in the area of interest. In typical cardiac imaging, tracers are used that accumulate in the well-perfused muscle tissue. The nuclear events are detected by a detector array 22.

Upon reception of a radiation event at the detector array 22, an event binning processor 24 sorts each event into an appropriate bin 26. In a preferred embodiment, there are twenty-four event bins 26. These represent three different respiratory cycle positions at each of the eight cardiac cycle positions. When an event is received, the event binning processor 24 notes the point in the respiratory cycle from the respiratory monitor 16 and the point in the cardiac cycle from the ECG monitor 18. From this information, the event binning processor 24 is able to sort out each radiation event into its appropriate bin 26. Optionally, the binning can be achieved by marking each event with an indicator of the corresponding points in the respiratory and cardiac cycles. The marking may be also achieved indirectly through coordinated time stamps of the events and outputs of the respiratory and cardiac monitors.

Once all of the desired events are collected, a reconstruction processor 30 reconstructs each bin of events into a separate image. Each of the twenty-four reconstructed images is reconstructed with relatively higher spatial resolution but may be high in noise if the count density is low. Each of the bins is essentially a snapshot of the heart, in the point of the cardiac and respiratory cycles that its counts were collected. If all of the events were constructed in a single image without cycle dependant binning, the single image would be blurred and degraded by the cardiac and respiratory movement.

Figure 2:
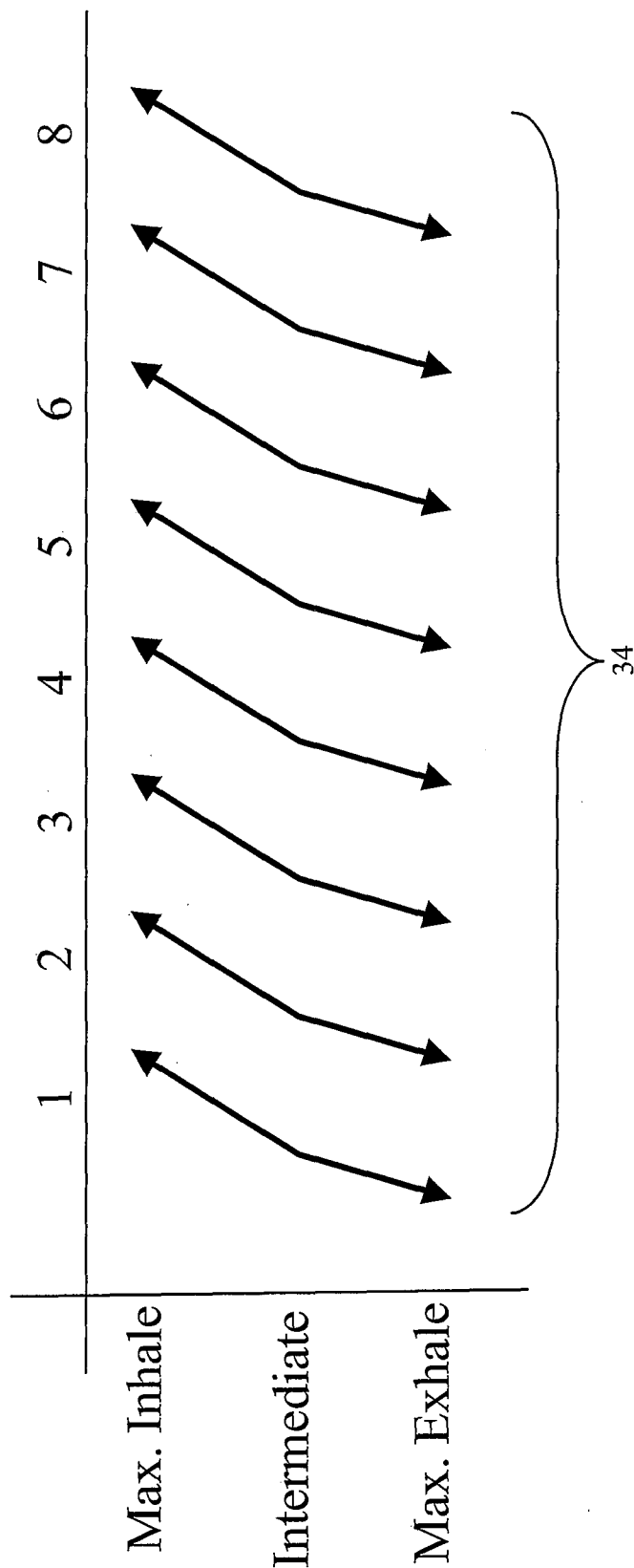
FIG. 2 is a vector field describing typical respiratory displacement.

Once all of the events in each of the event bins 26 are reconstructed into an image, the images are adjusted and combined. First, a respiratory adjustment processor 32 registers and combines the disparate respiratory component images of each cardiac phase. In the preferred embodiment, there are three images for each imaged point or phase in the respiratory cycle: one representing maximum inhale, one representing maximum exhale, and one representing an intermediate respiratory stage, tracked by the motion of the diaphragm as reported by the respiratory monitor 16. The motion caused by the respiratory cycle is virtually all translation in the cranial-caudal direction. Within each of the eight imaged cardiac phases the three images are virtually identical except for offsets in the cranial-caudal direction. The respiratory adjustment processor 32 compares the three images and determines a registration transform among the images, e.g., a translation, a rigid transformation, or an affine transform. In all cardiac phases, the respiratory shift should be the same. In one embodiment all cardiac phase images are used to determine a common rigid transform. Alternately, one or a few phases can be used to determine the transform for all phases. As yet another option, a transform is independently determined for each phase. For example, the respiratory adjustment processor 32 may use the sum of squared gray value differences as a similarity measure due to the mono-modal nature of the problem. In this manner, the respiratory adjustment processor 32 develops a respiratory transformation, which in the simplest case could be a translation vector 34, as depicted in FIG. 2, directly from the SPECT image data.

In the preferred embodiment, the respiratory adjustment processor includes a transformation routine 36 that transforms the maximum inhale and the maximum exhale images to overlay the intermediate image. Alternately the images can be brought into alignment in other points in the respiratory cycle, e.g. at one of the extremes. Once aligned, the three images within each one of the eight imaged cardiac phases are combined by a summation routine, (38) preferably in a linear summation of counts. Alternatively, either the maximum inhale or maximum exhale (or both) may be weighted more if the intermediate stage images are more blurred due to being collected over a wider range of movement. Adjusting and combining the images in each imaged cardiac phase according to the respiratory transformation creates a single image for each cardiac phase in which the spatial blur induced by respiration is removed. Because the combined image in each phase has more counts, e.g. three times as many, it has less noise than the originally collected cardiac and respiratory gated images. In the illustrated embodiment, the twenty four images are reduced to eight images, each in a different cardiac phase but in the same respiratory phase.

For comparable signal-to-noise properties of the reconstructed SPECT images for each heart phase, the thresholds can be chosen such that approximately the same number of the SPECT events falls into each of the respiratory bins. To minimize residual motion blur during the respective respiratory time interval at the resolution scale of the reconstructed SPECT images, longer data collection time intervals can be defined at maximum inhale and exhale, where the motion is minimal, and shorter collection time intervals at intermediate state(s) where the motion is greater. This will result in an uneven distribution of the SPECT events over the respiratory bins, but the original signal-to-noise ratio is retrieved once the images are combined. This is advantageous if the separate, respiratory phase-specific images are not useful for diagnostic purposes.

Alternately, at the cost of some SPECT event counts in the regions of fastest movement, the intermediate respiratory stage can be eliminated or greatly restricted since it has the highest residual variance. Thus, only the maximum inhale and exhale (and possibly one or more unblurred intermediate respiratory stages) can be acquired, transformed, and summed.

After the twenty-four images are combined into eight cardiac phase images in the illustrated embodiment, the remaining eight images can be combined into a single SPECT image. With continuing reference to FIG. 1, an operator designates which point of the cardiac cycle he/she would like to see in the final image at a user interface 40. Alternatively, a reference phase may be used as a default. When the eight (respiratory combined) cardiac phase images have been established, a cardiac adjustment processor 42 retrieves the latest patient specific cardiac model from the cardiac model database 13. The cardiac adjustment processor 42 identifies which of the eight images (if any) corresponds with the user input cardiac phase. The cardiac adjustment processor includes a routine 44 that analyzes the patient specific cardiac model to generate transforms that transform each of the cardiac phase images into the user selected phase. The transforms typically include translation, rotation, enlarging, (or shrinking), summing, and warping of the cardiac phase images to bring them into alignment with the selected phase.

More specifically, the transform generating routine 44 of the cardiac adjustment processor 42 first generates a point-to-point correspondence of the SPECT image data into the patient specific cardiac shape and motion model. Here, the patient-specific cardiac shape model corresponding to the selected cardiac phase is registered or aligned with the respiratory-motion compensated SPECT image for the same cardiac phase to establish point correspondence. A rigid transformation is sufficient for this task, if the geometry of the two scans is correct (no scaling, shearing, or warping). The patient-specific motion map as derived from the cardiac modeling scan is then applied to the corresponding points in the respiratory-motion compensated SPECT images of the different cardiac phases. The motion vector fields from the patient-specific motion model are interpolated to determine the inverse of the motion vector fields for each pixel of the reconstructed (and respiratory averaged) SPECT images from its actual phase to the selected cardiac phase. A transform routine 46 operates on each of the cardiac phase images to transform it to the selected cardiac phase and a combining routine 48 combines, e.g. sums, the transformed cardiac phase images in the selected phase. Of course, the transformed images can be weightedly combined. For example, images which are transformed the least can be weighted more that those that are transformed the most.

Since CT (or other modality) data is being used, there are other anatomical structures present that are unavailable in the SPECT image. This provides more reference points to gauge the motion of the heart.

This process effectively removes all components of motion due to both the cardiac and respiratory cycles. Once the images are aligned, they are combined into a single diagnostic image. Alternatively, the cardiac adjustment processor can perform the above process to a plurality of selected cardiac phases. This way, the user could have any number of cardiac phases in the combined format, or a cine presentation of the combined images.

The respiratory adjustment processor 32 and the cardiac adjustment processor 42 may be defined within a single computer or distributed among a variety of processing modules.

Once the combined SPECT image(s) is acquired, it is presented to the user on the user interface 40, or alternatively, on a separate output device 50 such as a dedicated monitor, palm device, hard copy printout, e-mail account, intranet web server, or the like. The completed images are also stored in an image archive 52 for convenient recall and study at a later time.

As stated before, the illustrated embodiment has been described utilizing twenty four bins at eight cardiac phases in each of three respiratory phases, but the number of bins and the number of cardiac and respiratory phases can be more or less. It is neither intended that the cardiac cycle be limited to eight segments, nor that the respiratory cycle be limited to three segments.

Figure 3:
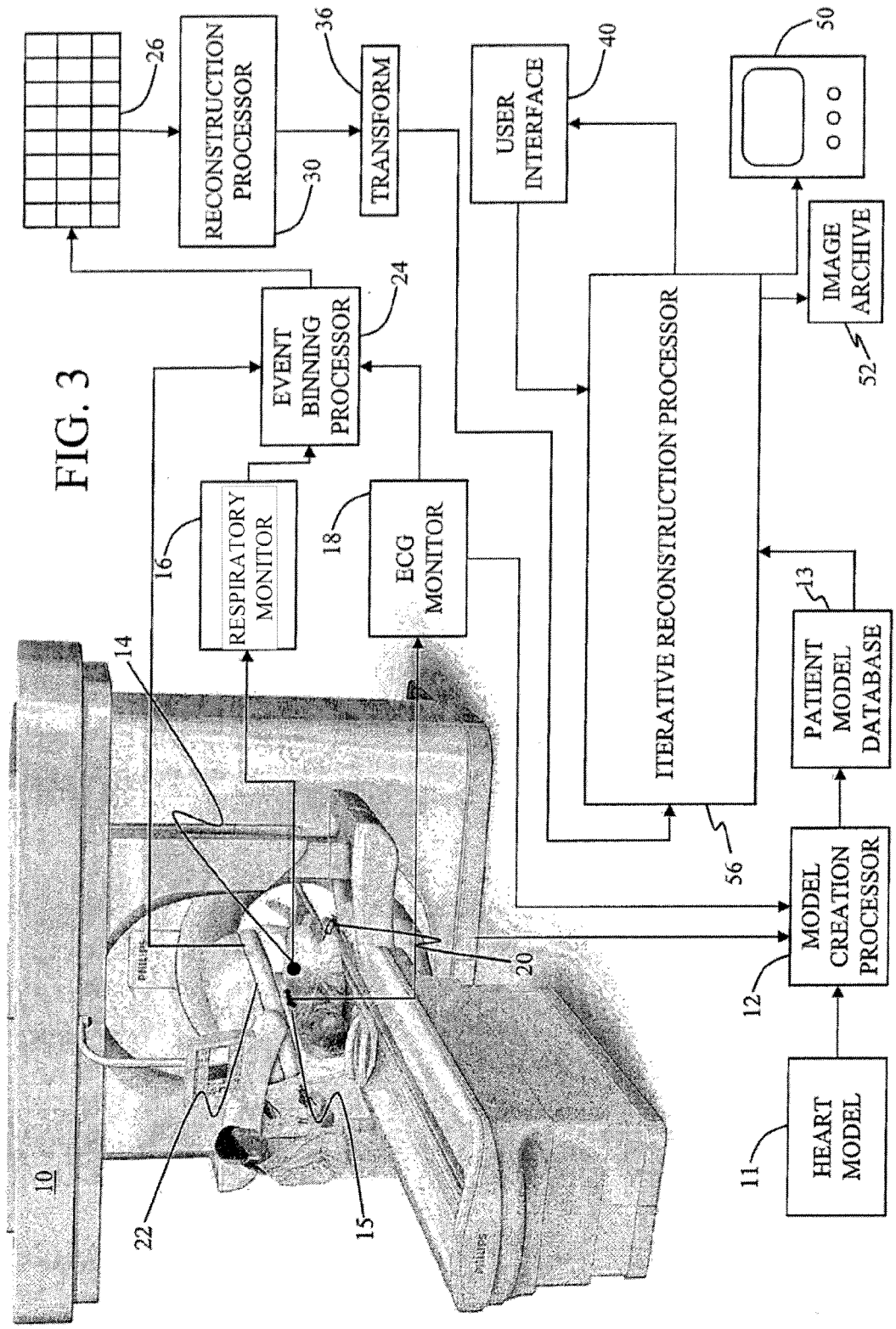
FIG. 3 is a diagrammatic illustration of a SPECT/CT system utilizing an iterative reconstruction; and, FIG. 4 is a detailed flow chart of the data processing performed during iterative reconstruction.
Figure 4:
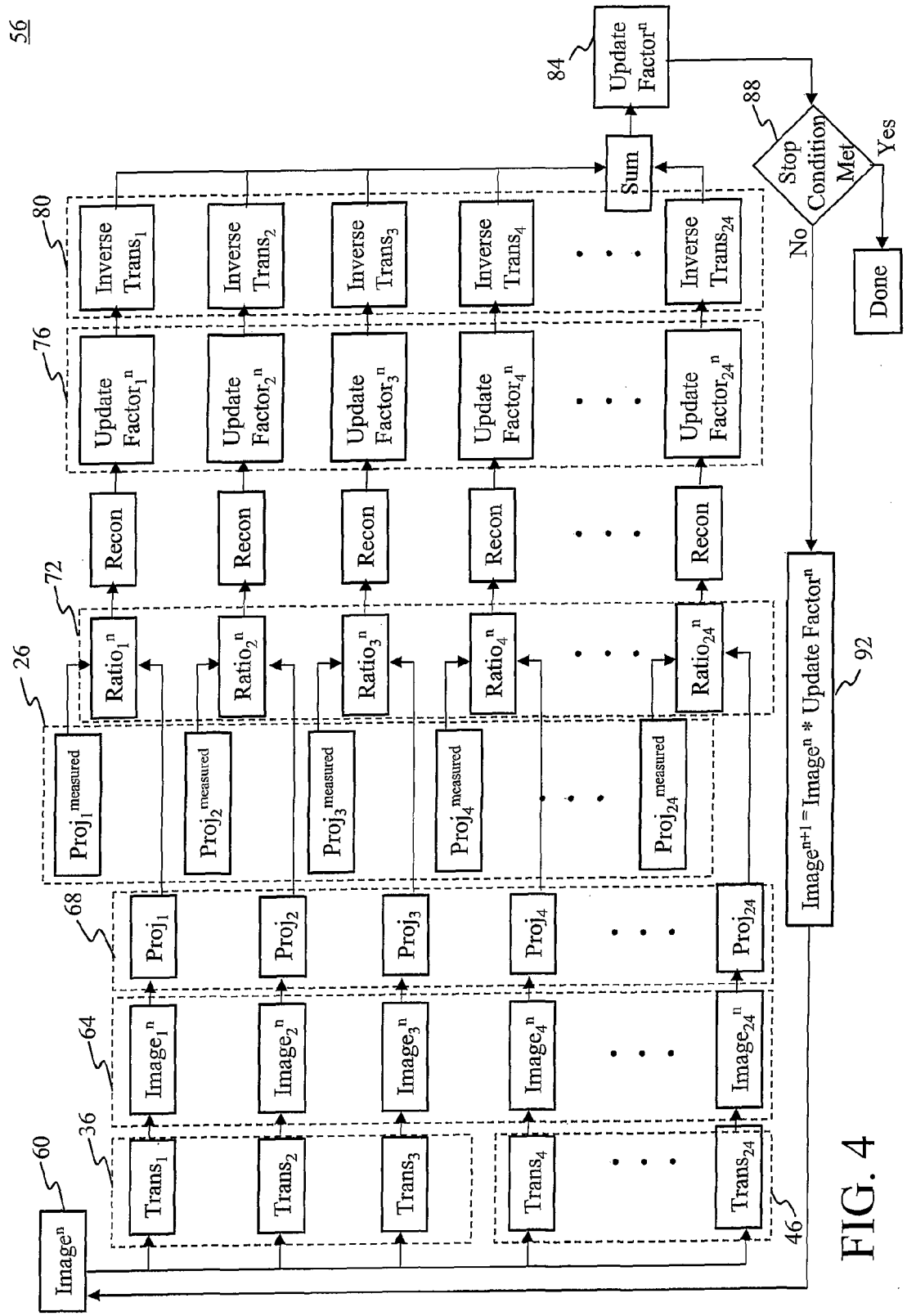

In an alternate embodiment, the respiratory adjustment processor 32 and the cardiac adjustment processor 42 may be replaced by an iterative reconstruction processor 56 as depicted in FIG. 3 and FIG. 4. The current image estimate 60 is transformed according to the three respiratory transformations 36 and the eight cardiac transformations 46 to generate all twenty four image estimates 64. These image estimates are then projected to generate twenty four projection estimates 68 that are then compared to the measured projections in the twenty-four event bins 26 to generate the twenty four ratios 72. These ratios 72 are reconstructed to generate twenty four update factors 76, the inverse respiratory and cardiac transforms 80 are applied, and the result summed to generate an overall update factor 84. If the stop condition 88 is met, (e.g., maximum number of iterations done, or change in update factor less than some tolerance), the current image 60 is the final image. If the stop condition 88 is not met, a new image estimate is generated 92 and the process continues.

In an alternate embodiment, the preliminary scan is not performed to create the patient specific cardiac motion model. Instead, a generic cardiac motion model is used. This embodiment carries the advantage of eliminating the preliminary scan at the cost of the individualized data. This method would produce faster results with less accuracy.

In such embodiments, it is advantageous to create a database from a sufficiently large number of patients. In some embodiments, the current scan of a specific patient can be used as an additional patient in the patient pool, thereby allowing for update of the data based on a larger population. The database is derived using gated acquisition with a fixed number of gates. Ideally, the number of gates used would match the specific current study, although pooling of gates and other such methods can also be used. The database may be derived at a different time and location and may use different imaging equipment. For example, it may be advantageous to image the background patient for the database on a high-resolution system, which may not be available at the site of the current study.

After acquisition, the image data is reconstructed for each gate and transformation matrices are estimated by mapping each gate to a reference gate. As with any of the methods described above, the transformation matrices can be formed using principal component analysis (PCA), clustering algorithms, or any other acceptable method.

Once the database has been derived, a current study can use the database to correct for motion. For the current study, gated image data is acquired and reconstructed into individual gated images. The transform matrices between the gates images are then estimated using the database of estimated transformation matrices. For PCA, this can be formulated as follows:

Denote the transformation matrix to be estimated with $T_{patient}$, and the PCA basis of transformation matrices estimated in database by $T_i$, then $T_{patient}$ can be written:

$$T_{patient} = \sum_{i=1}^{cutoff} \lambda_i T_i$$

Therefore, only the expansion coefficients $\lambda_i$ have to be estimated from the patient data (instead of the transformation matrix itself). It is assumed that a small number of expansion coefficients (e.g. 3-5 or even less) is sufficient to represent the transformation matrix to be estimated. Moreover, the number of expansion terms may be adjusted to the count statistics of the acquisition. For example, only one expansion term may be appropriate in case of extremely low count statistics. If more data becomes available, the number of coefficients may be increased.

For clustering algorithms, the task is to find the cluster of transformation matrices which is most "similar" to the transformation matrix to be estimated, and use a representative of the cluster as estimate for the unknown transformation matrix.

Once the estimated transform matrices have been estimated, the image data can be corrected to compensate for motion. In this illustrative approach, the number of parameters to be estimated from the new patient data is reduced. Furthermore, such methods can be used with relatively low count statistics since information is used from the background patient database. Consequently the number of gates can be increased, thereby allowing for finer time resolution for modeling the motion cycle.

In some embodiments, a patient specific cardiac motion model can be constructed from the high resolution scan without melding with a generic heart model. In this embodiment, a mapping of corresponding points is performed in each phase. A manual mapping procedure is labor intensive, but can be very accurate.

In other embodiments, a Doppler ultrasound is used to generate a direct motion vector field of the motion of the heart due to respiration. In another embodiment, the cardiac modeling scan is conducted after the nuclear scan.

It should be appreciated that the motion compensation described in this application is not limited to cardiac, but rather cardiac motion is merely an illustrative example. For instance, respiratory motion can be accounted for using the methods described above to provide transformation matrices for any organ or region of interest. In embodiments that use a motion model database, the database can be populated based on respiratory motion alone or in combination with local motion of the region of interest, such as, for example, the heart. Consequently, a database can be derived for each individual region of interest.

Another optional feature for systems that use the methods described above, would be a user interface that allows the physician to choose between different motion compensation options. For example, the user interface can allow for "traditional" gated motion compensation, specific patient model based motion compensation, or general database based motion compensation. Any of those methods can account solely for respiratory motion or can be combined with cardiac contractile motion compensation. It should be appreciated that the methods described herein may be further applied to other physiological motion, including, but not limited to, peristaltic motion. In embodiments that allow for user selection of the motion compensation method, the user interface would provide for a selection of the desired motion compensation method, such as, for example, by indication with icons or a pull-down list.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method of respiratory and cardiac movement compensated diagnostic imaging comprising:
   monitoring respiratory activity of a subject during an imaging scan with a first imaging modality;
   monitoring cardiac activity of the subject during the scan;
   binning raw image data acquired during the scan in accordance with its occurrence in both respiratory and cardiac phases;
   reconstructing the binned raw data into a plurality of heart images in each of a plurality of respiratory and cardiac phases;
   transforming images of the plurality of images which have different respiratory phases into a series of respiratory compensated images at the plurality of cardiac phases and at a selected common respiratory phase;
   transforming the series of respiratory compensated images in accordance with a heart shape and motion model to generate a series of cardiac and respiratory compensated images in a selected common cardiac phase and the selected common respiratory phase, wherein the heart shape and motion model models the entire shape of a heart; and,
   combining the images in the selected common cardiac and respiratory phases.

2. The method according to claim 1 further including:
   generating images of a heart of a subject in each of a plurality of cardiac phases with a second imaging modality;
   fitting a generic heart shape and motion model to the generated heart images to generate a subject specific heart shape and motion model.

3. The method according to claim 2, wherein the second imaging modality is nuclear.

4. The method according to claim 3, wherein the first imaging modality is cardiac gated CT.

5. The method according to claim 4, wherein the first plurality of images is generated from CT data collected during a single breath hold.

6. The method according to claim 2, wherein the plurality of first imaging modality images are in a common respiratory phase.

7. The method according to claim 1, wherein the plurality of first imaging modality images includes images in each of N cardiac phases and M respiratory phases, where N and M are plural integers, such that the plurality of first imaging modality images includes N×M images.

8. The method according to claim 7, wherein the N respiratory phases include a maximum inhale phase and a maximum exhale phase.

9. The method according to claim 1, wherein generating the plurality of first imaging modality images includes:
   acquiring data with cardiac and respiratory gating; and,
   reconstructing data with common respiratory and cardiac phases into the plurality of first imaging modality images.

10. The method according to claim 1 wherein the plurality of generated heart images are current estimate heart images and iteratively repeating the following steps until a stop condition is met:
    performing the first and second transforming steps with the estimate heart images to generate a series of cardiac and respiratory compensated estimate images;
    projecting the series of cardiac and respiratory compensated estimate images to generate a series of projection estimates;
    comparing the projection estimates with measured projections to generate a series of ratios;
    reconstructing the ratios to generate a series of update factors;
    applying inverses of the first and second transforming steps to generate an overall update factor.

11. A diagnostic imaging apparatus including a processor programmed to perform the method of claim 1.

12. The method according to claim 1, further including:
    generating images of a heart of a subject in each of the plurality of cardiac phases with a second imaging modality, the second imaging modality different than the first imaging modality, and the plurality of heart images being of the heart of the subject;
    fitting a generic heart shape and motion model to the generated images to generate the heart shape and motion model, the heart shape and motion model specific to the subject;
    for each of the plurality of cardiac phases, combining images of the series of respiratory compensated images of the cardiac phase into a combined respiratory compensated image;
    transforming the combined respiratory compensated images of the plurality of cardiac phases in accordance with the heart shape and motion model to generate the series of cardiac and respiratory compensated images in the selected common cardiac phase and the selected common respiratory phase; and,
    combining the images of the series of cardiac and respiratory compensated images.

13. The method according to claim 1, further including:
    generating a database of gated transform matrices based on image data from a patient pool, the image data including image data of the plurality of heart images, and the gated transform matrices compensating for respiratory motion;
acquiring gated image data for a current image to be motion corrected;
reconstructing the image data to form gated images;
using the transformation matrices collected in the database to estimate a current set of transformation matrices accounting for respiratory motion; and
generating a current motion-compensated image based on the current set of transform matrices.

14. A diagnostic imaging apparatus comprising:
a respiratory monitor which monitors respiratory activity of a subject during an imaging scan;
a cardiac monitor which bins raw image data acquired during the scan in accordance with its occurrence in both respiratory and cardiac phases and monitors cardiac activity of the subject during the scan;
a first modality scanner that reconstructs the binned raw data to generate a plurality of volumetric heart images in each of a plurality of respiratory and cardiac phases, wherein each of the plurality of volumetric heart images are three-dimensional;
a respiratory adjustment processor that, for each of the plurality of cardiac phases, transforms volumetric images of the plurality of volumetric images which share the cardiac phase and have different respiratory phases into a series of respiratory compensated volumetric images at a selected common respiratory phase, the selected common respiratory phase common to the plurality of cardiac phases;
a respiration summing routine that, for each of the plurality of cardiac phases, combines the volumetric images of each series of respiratory compensated volumetric images into a combined respiratory compensated volumetric image;
a cardiac transforming routine that transforms the combined respiratory compensated volumetric images of the plurality of cardiac phases in accordance with a heart shape and motion model to generate a series of cardiac and respiratory compensated volumetric images in a selected common cardiac phase and the selected common respiratory phase, wherein the heart shape and motion model models a three-dimensional volume of a heart; and,
a cardiac summing routine that combines the images of the series of cardiac and respiratory compensated volumetric images.

15. The diagnostic imaging apparatus according to claim 14, further including:
a cardiac model generating scanner that generates images of a heart of a subject in each of a plurality of cardiac phases with a first imaging modality;
a model creation processor that fits a heart shape and motion model to the generated heart images to generate a subject specific heart movement model.

16. An image reconstruction processor for use in conjunction with cardiac nuclear imaging procedures comprising:
a reconstruction processor which receives signals indicative of respiratory activity and cardiac activity during an imaging scan, bins raw data acquired during the imaging scan based on the respiratory and cardiac activity, and reconstructs the binned raw data into a plurality of heart images;
a respiratory adjustment processor that receives the plurality of heart images with differing respiratory phases and differing cardiac phases and adjusts the images of differing respiratory phases and cardiac phases into a series of heart images with a common respiratory phase and the differing cardiac phases;
a cardiac adjustment processor that receives the series heart images from the respiratory adjustment processor and adjusts the series of heart images into a common cardiac phase and the common respiratory phase.

17. The image reconstruction processor according to claim 16, wherein the respiratory adjustment processor includes:
a transformation routine that transforms images of different respiratory phases and the same cardiac phase to spatially overlay each other.

18. The image reconstruction processor according to claim 16, wherein the cardiac adjustment processor includes:
a transform calculating routine that creates a transform for warping, translating, rotating, and zooming the series images at the differing cardiac phases into the common cardiac phase.

19. The image reconstruction processor according to claim 18, wherein the cardiac adjustment processor further includes:
a transform application routine that applies the transform to each image of the series images to generate a series of images with the common respiratory phase and the common cardiac phase.

20. A diagnostic imaging apparatus, comprising:
the image reconstruction processor according to claim 16;
a display for displaying images; and,
a user interface comprising:
a motion compensation selector, wherein the motion compensation selection mechanism allows the user to select a motion compensation method.

21. The diagnostic imaging apparatus according to claim 20, wherein the selectable motion compensation method includes at least one of a specific patient model based motion compensation method and general database based motion compensation method.

22. The diagnostic imaging apparatus according to claim 20, wherein the selectable motion compensation method includes both a specific patient model based motion compensation method and general database based motion compensation method.

23. A diagnostic imaging apparatus comprising:
a respiratory monitor that monitors respiratory activity of a subject during imaging scans with a first imaging modality and a second imaging modality;
a cardiac monitor which monitors cardiac phases of the subject during the imaging scans;
at least one processor programmed to:
receive the monitored respiratory and a plurality of cardiac phases and raw data acquired by the first imaging modality and the second imaging modality during the imaging scans and bins the raw image data in accordance with the respiratory and cardiac phases;
reconstructs the binned raw data into a plurality of heart images of the subject corresponding to the plurality of cardiac phases;
fit a generic heart shape and motion model to the plurality of heart images of the first imaging modality to generate a heart shape and motion model, the heart shape and motion model specific to the subject, wherein the heart shape and motion model models the entire shape of a heart;
generate a plurality of cardiac compensated images in a selected common cardiac phase using the heart shape and motion model and the plurality of heart images of the second imaging modality; and,
combining the plurality of cardiac compensated images.

24. The diagnostic imaging apparatus according to claim 23, wherein the plurality of heart images of the second imaging modality include a plurality of respiratory phases, wherein generating the plurality of cardiac compensated images includes:

transforming the plurality of heart images of the second imaging modality into a series of respiratory compensated images at the plurality of cardiac phases and at a selected common respiratory phase; and, transforming the series of respiratory compensated images in accordance with the heart shape and motion model to generate the plurality of cardiac compensated images, the plurality of cardiac compensated images being in the selected respiratory phase.

25. The diagnostic imaging apparatus according to claim 24, wherein generating the plurality of cardiac compensated images further includes:

for each of the plurality of cardiac phases, combining images of the series of respiratory compensated images of the cardiac phase into a combined respiratory compensated image; and, transforming the combined respiratory compensated images of the plurality of cardiac phases in accordance with the heart shape and motion model to generate the plurality of cardiac compensated images in other selected respiratory phases.

26. A method of compensating for respiratory and cardiac movement in diagnostic imagine reconstruction comprising:

monitoring respiratory activity of a subject during a nuclear imaging scan and creating a respiratory movement vector;

monitoring cardiac activity of the subject during the scan;

binning raw image data acquired during the scan in accordance with its occurrence in both respiratory and cardiac phases;

reconstructing the binned raw data into a plurality of images;

transforming the images in accordance with the respiratory movement vector;

adjusting the resultant transformed images in accordance with a heart shape and motion model; and, combining the adjusted images.

\* \* \* \* \*